United States Patent [19]

Yagata

[11] Patent Number: 4,635,644
[45] Date of Patent: Jan. 13, 1987

[54] ULTRASONIC APPLICATOR

[75] Inventor: Yukihiro Yagata, Kawachinagano, Japan

[73] Assignee: Hitachi Medical Corporation, Tokyo, Japan

[21] Appl. No.: 714,822

[22] Filed: Mar. 22, 1985

[30] Foreign Application Priority Data

Jul. 24, 1984 [JP] Japan .................. 59-153801

[51] Int. Cl.⁴ ............................. A61B 10/00
[52] U.S. Cl. ................................. 128/660
[58] Field of Search ............... 128/660, 661, 24 A

[56] References Cited

U.S. PATENT DOCUMENTS

| | | | |
|---|---|---|---|
| 4,029,084 | 12/1975 | Soldner | 128/660 |
| 4,469,106 | 9/1984 | Harui et al. | 128/660 |
| 4,475,553 | 10/1984 | Yamaguchi et al. | 128/660 |
| 4,527,569 | 7/1985 | Kolb | 128/660 |
| 4,542,747 | 9/1985 | Zurinski et al. | 128/660 |

Primary Examiner—Kyle L. Howell
Assistant Examiner—Francis J. Jaworski
Attorney, Agent, or Firm—Antonelli, Terry & Wands

[57] ABSTRACT

An ultrasonic applicator for an ultrasonic-echo planigraphic imaging apparatus has a plurality of ultrasonic transducer elements arranged in row on a living body application surface of the ultrasonic applicator. The ultrasonic applicator comprises a puncturing cannula guiding slot along a plane included within an applicator body and extending in a longitudinal direction, ultrasonic transducer elements arranged on both sides of the slot, and a puncturing cannula guiding mechanism for guiding a puncturing cannula through the slot to a point to be examined. The puncturing cannular inserted in the living body is exactly indicated on an indicator and the location of the puncturing cannula may readily be confirmed.

4 Claims, 10 Drawing Figures

FIG. I
PRIOR ART
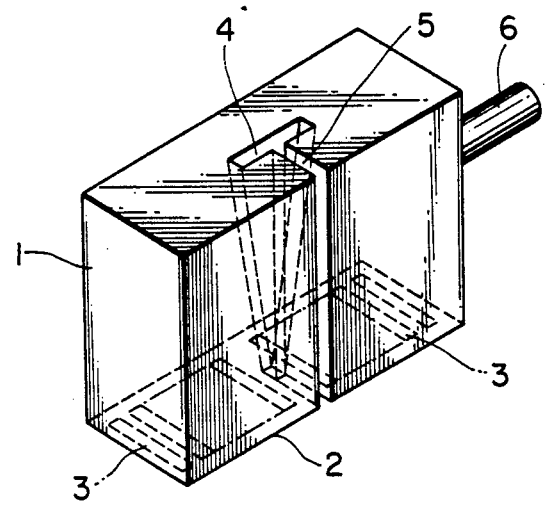
FIG. 2
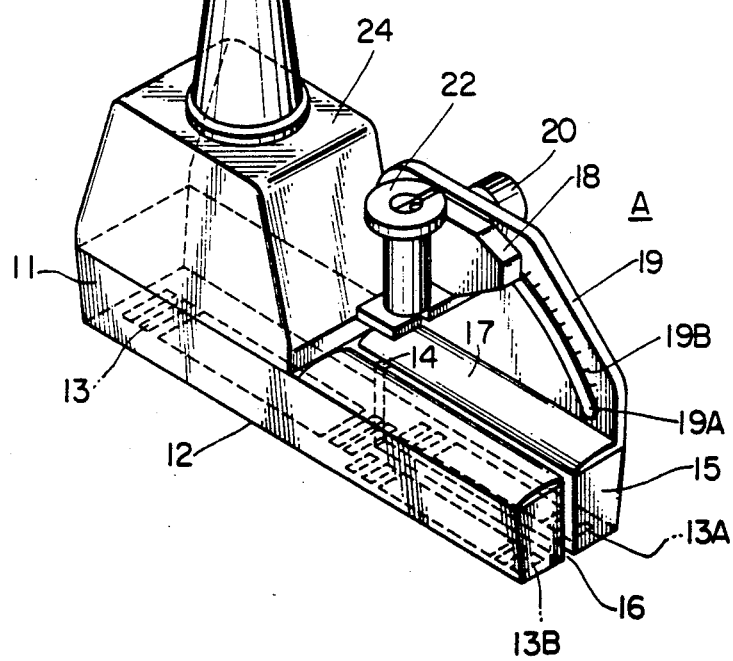

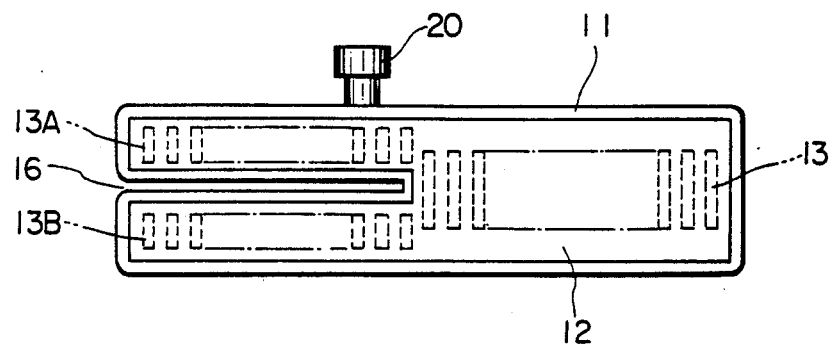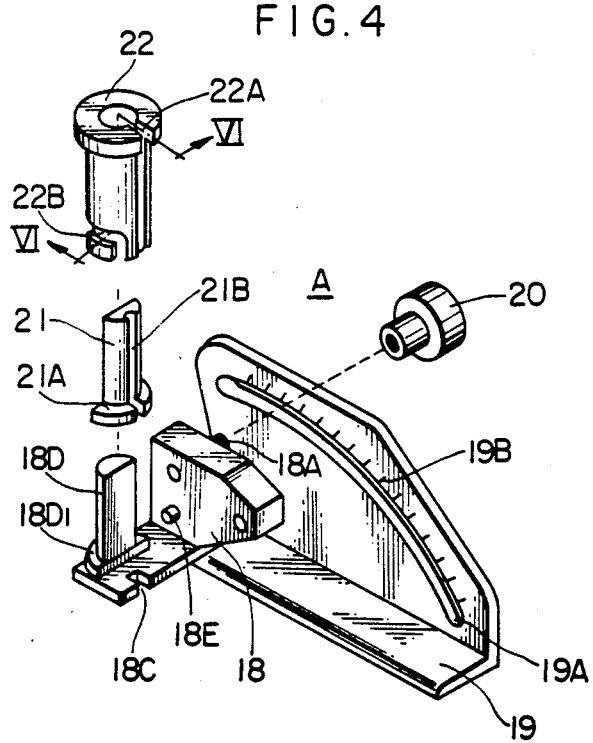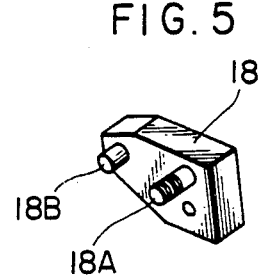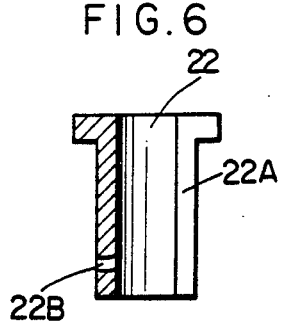

ULTRASONIC APPLICATOR

BACKGROUND OF THE INVENTION

1. Field of the Invention

The present invention relates to an ultrasonic applicator, and more particularly to an ultrasonic applicator for an ultrasonic-echo planigraphic imaging apparatus used when a puncturing cannula or needle is inserted into a tissue, of a living body, to be examined as in a biopsy and a blood vessel photograph method using X-ray photographing.

2. Description of the Prior Art

A biopsy examination is conducted for the purpose of picking out a tissue or a body fluid out of organs of a living body such as a liver, and a kidney by a suitable puncturing cannula or needle for medical examination. Also, a blood vessel photographing method refers to X-ray photographing by inserting the puncturing cannula into a blood vessel for injecting a contrast medium thereinto.

In such cases, if, in order to pick out a desired tissue of the living body for the medical examination or to prevent a mistake in inserting the cannula upon the injection of the contrast medium, the desired point of the living body or the blood vessel is indicated in an ultrasonic-echo planigraphical manner on a suitable indicator and the cannula is inserted thereto in accordance with the ultrasonic-echo planigraphic image, then a desired puncturing may readily be attained. Therefore, for that purpose, an ultrasonic applicator for puncturing is utilized.

For instance, as an ultrasonic applicator for puncturing, there has been often used a penetration type applicator in which a puncturing cannula guiding slot is formed substantially in the central portion of the applicator body as disclosed in U.S. Pat. No. 4,029,084 (German equivalent DE-GM No. 74 42 294).

More specifically, as shown in FIG. 1, in the prior art ultrasonic applicator puncturing probe, a number of ultrasonic transducer elements 3 are arranged parallel to one another along the length of an application surface 2 of the applicator body 1. A puncturing cannula inserting slot 4, for insertion of the cannula, through which the cannula is inserted into the tissue or the like to be examined is formed substantially in the central portion of the applicator body 1. The puncturing cannula inserting slot 4 is defined by a trapezoidal space which is tapered toward the application surface 2. A cannula guiding slot 5 for guiding the puncturing cannula into the inserting slot 4 is formed so as to penetrate from the cannula inserting slot 4 to a front surface of the applicator body 1. The ultrasonic transducer elements 3 are connected through a connector cable 6 to a suitable control means.

However, in the conventional penetration type puncturing ultrasonic applicator, since the cannula inserting slot 4 is provided in the central portion of the applicator body 1, the ultrasonic transducer elements 3 which would otherwise be provided at the opening portion of the slot 4 have been removed. As a result, the ultrasonic energy is diffused at the portion where the ultrasonic transducer elements are not provided, thereby forming an inevitable loss portion. Therefore, there would be generated a stripe-shaped defect (low brightness) on the image indicator for indicating the ultrasonic-echo planigraphic image.

In order to carry out the basic puncturing operation in which the cannula or needle is carried through a minimum distance up to a desired point of the living body to be examined, the cannula must be advanced through the stripe-shaped defect, so that it is difficult to confirm the tip end of the cannula and it is also difficult to exactly insert the cannula into the point of the living body to be examined.

Also, in the conventional applicator, since the insertion opening which is the end portion of the cannula inserting slot 4 of the ultrasonic applicator for inserting the cannula is made small at a single location, it is difficult to render the insertion opening to be aligned with the point to be examined. Furthermore, if the point to be examined is desired to be changed after the puncturing operation, it is necessary to again align the applicator to another point to be examined. The conventional applicator needs such various steps and is troublesome to handle.

SUMMARY OF THE INVENTION

In order to overcome the above-noted defects, an object of the present invention is to provide a puncturing ultrasonic applicator in which a puncturing cannula inserted into a tissue or the like of the living body is exactly indicated in an indicator and the location of the cannula may readily be confirmed.

According to a typical aspect of the present invention, an ultrasonic applicator for an ultrasonic-echo planigraphic imaging apparatus having a number if ultrasonic transducer elements arranged parallel to one another on an application surface of a living body comprises a puncturing cannula guiding slot along a plane included within an applicator body and extending in a longitudinal direction, no more than one half of the ultrasonic transducer elements also arranged on both sides of the slot together with the transducer elements provided on the undivided surface, and means provided on the upper portion of the slot for guiding a puncturing cannula to a point to be examined through the slot, whereby the puncturing cannula inserted in the living body is exactly indicated on an indicating means and the location of the puncturing cannula may readily be confirmed.

BRIEF DESCRIPTION OF THE DRAWINGS

In the accompanying drawings:

FIG. 1 is a perspective view illustrating disadvantages inherent in the conventional penetration type ultrasonic probe for inserting a cannula;

FIGS. 2 through 8 are views illustrating an ultrasonic applicator for an ultrasonic-echo planigraphic imaging apparatus in accordance with a first embodiment of the invention;

FIG. 2 is a perspective view showing the ultrasonic applicator as a whole;

FIG. 3 is a plan view as seen from the application sided surface of the ultrasonic applicator;

FIG. 4 is an exploded view showing a specific structure of a puncturing cannula guiding mechanism A shown in FIG. 2;

FIG. 5 is a perspective view of a puncturing cannula guiding member shown in FIG. 4, as viewed from the rear side thereof;

FIG. 6 is a cross-sectional view taken along the line VI—VI in a fastening outer sleeve shown in FIG. 4;

FIG. 7 is a plan view, as seen from the application sided surface, specifically illustrating the arrangement of the ultrasonic transducer elements of the ultrasonic probe shown in FIG. 2;

FIG. 8 is a plan view of the ultrasonic probe shown in FIG. 2, as viewed from above;

DETAILED DESCRIPTION OF THE PREFERRED EMBODIMENTS

Figure 7:
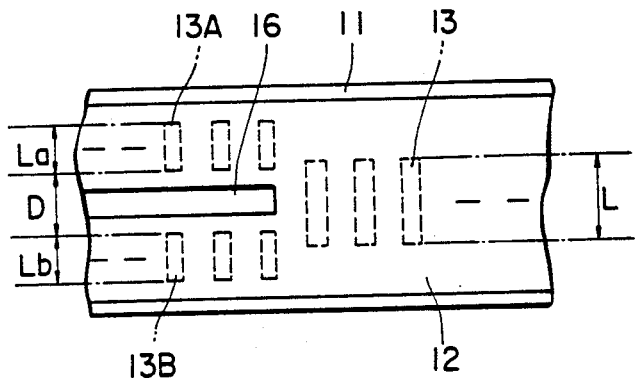

The present invention will now be described in detail with reference to the accompanying drawing in which the same reference numerals designate the like components or parts.

In FIGS. 2 to 8, an applicator body of an ultrasonic-echo planigraphic imaging apparatus is generally designated by reference numeral 11, and a number of ultrasonic transducer elements 13 are arranged parallel to one another in a predetermined row on an application surface 12, to be brought into contact with a living body. In the applicator body 11, there is formed a puncturing cannula guiding slot 16 extending from a central portion to one sided surface 15 of the applicator body 11. The puncturing cannula guiding slot 16 defines a planar thin space which intersects with the application surface 12 of the applicator body 11 along its longitudinal direction, that is, a thin parallelepiped space which presses from the application surface 12 to an opposite upper surface 17.

Half or less of the number of the ultrasonic transducer elements 13 arranged parallel to one another in the predetermined row on the application surface 12 are each divided into two groups of ultrasonic transducer elements 13A and 13B by the puncturing cannula guiding slot 16 as best shown in FIGS. 2 and 3. All of the thus divided ultrasonic transducer elements 13A and 13B have the same length and the same width, and are associated to form respective pairs by a suitable electric connection with the pair of elements being actuated simultaneously with each other. A spaced distance D between the respective ultrasonic transducer elements 13A and 13B grouped into two groups by the puncturing cannula guiding slot 16 is shorter than a length L of the other normal ultrasonic transducer elements 13 as shown in FIG. 7. Since the spaced distance D between the ultrasonic transducer elements 13A and 13B sometimes causes the ultrasonic characteristics and the S/N ratio to be degraded, as shown in FIG. 7, longitudinal length La and Lb of the respective ultrasonic transducer elements 13A and 13B are increased in accordance with the spaced distance D, so that an area obtained by adding the respective effective areas of the paired ultrasonic transducer elements 13A and 13B is somewhat larger than an effective area of the ultrasonic transducer element 13. In other words, the longitudinal lengths of the ultrasonic transducer elements 13A and 13B and the ultrasonic transducer elements 13 are selected so that a sensitivity of the ultrasonic transducer elements 13A and 13B is substantially the same as that of the ultrasonic transducer elements 13. For example, the spaced distance D between the ultrasonic transducer elements 13A and 13B is 5 mm, the longitudinal length L of the ultrasonic transducer elements 13 is 7 mm and the longitudinal length L of the ultrasonic transducer elements 13A and 13B is 4 mm, respectively. With such an arrangement having the thus specified dimensions, the applicator may be used practically essentially without any adverse effect on an image quality of the sectional image while the sonic characteristics and the S/N ratio are only somewhat deteriorated.

At an upper portion of the above-described puncturing cannula guiding slot 16, there is provided a puncturing cannula guiding mechanism generally designated by reference character A. The cannula guiding mechanism A comprises a support plate 19 mounted on the upper portion of the applicator body 11 by a fastening means such as screws for carrying movably a puncturing cannula guiding member 18. In the support plate 19, there is formed a puncturing angle adjusting elongate hole 19A for setting a puncturing angle of the cannula. Provided in a circumferential portion of the puncturing angle adjusting elongate hole 19A is an angular scale 19B for indicating a vertical position through a position of an angle of 40° with respect to the application surface 12.

As shown in FIGS. 4 through 6, a fixed pin 18A and a support pin 18B are implanted in the puncturing guiding member 18 and are both slidably inserted into the puncturing cannula angle adjusting elongate hole 19A formed in the support plate 19. The puncturing cannula guiding member 18 may be fixed to the support plate 19 by fastening a fastening screw 20 to the fixed pin 18A. An outer sleeve fixing pin 18E is provided on the opposite side of the puncturing cannula guiding member 18. Mounted on the puncturing cannula guiding member 18 is a support member having therein a slit 18C, having a length of approximately 5 mm, into which the cannula is to be inserted, and a post 18D which is in the form of a semi-cylinder. The post 18D has an enlarged portion 18D$_1$ at its lower end. A puncturing cannula introducing member 21 for inserting the cannula is detachably brought into intimate contact with a planar portion of the post 18D. The puncturing cannula introducing member 21 is in the form of a semicylinder and has an enlarged portion 21A at its lower end. The enlarged portion 21A is formed on the puncturing cannula introducing member 21 for the purpose of preventing the puncturing cannula introducing member 21 from being removed apart from the puncturing cannula guiding member 18 when set upside down. A puncturing cannula introducing groove 21B is formed on the cylindrical side of the puncturing cannula introducing member 21. Since the width of the puncturing cannula introducing groove 21B is determined in accordance with a diameter of the cannula to be used, it is preferable that about ten kinds of the puncturing cannula introducing members 21 be prepared. A maximum diameter of the puncturing cannula used recently is approximately 2.16 mm.

The puncturing cannula introducing member 21 is held by a fastening outer sleeve 22 by bringing the planer portion of the puncturing cannula introducing member 21 into intimate contact with the planar portion of the post 18D of the above-described puncturing cannula guiding member 18. In the fastening outer sleeve 22, there are provided a puncturing cannula introducing groove 22A for attaching or detaching the puncturing cannula and a mounting hole 22B for engagement with the outer sleeve fixing pin 18E of the puncturing cannula guiding member 18.

The operation of the ultrasonic probe for the ultrasonic-echo planigraphic imaging apparatus in accordance with the first embodiment of the invention will now be described.

Figure 8:
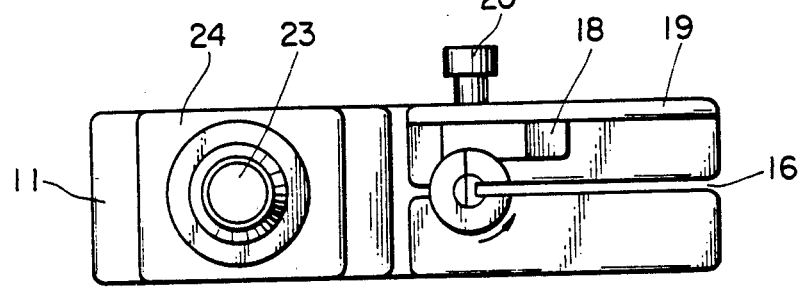

Referring again to FIGS. 2 through 8, the planar portion of the post 18D of the puncturing cannula guiding member 18 is brought into intimate contact with the planar portion of the puncturing cannula introducing member 21, and then the fastening outer sleeve 22 is set on the members 18 and 21, thereby holding the puncturing introducing member 21. Under such a condition, the mounting hole 22B provided in the fastening outer sleeve 22 is engaged with the outer sleeve fixing pin 18E of the puncturing cannula guiding member 18 so that the fastening outer sleeve 22 is fixed to the puncturing cannula guiding member 18. Then, as best shown in FIG. 8, the puncturing cannula guiding groove 21B of the puncturing cannula introducing member 21 is aligned with the puncturing cannula introducing groove 22A of the fastening outer sleeve 22, the puncturing cannula is inserted into the aligned grooves, and the fastening outer sleeve 22 is rotated counterclockwise (or clockwise), thereby performing the mounting operation of the puncturing cannula. Subsequently, the ultrasonic-echo planigraphic imaging apparatus is made operative to form an ultrasonic sectional image on an indicating means. While the ultrasonic sectional image on the indicating means is being watched, the fastening screw 20 is loosened and the puncturing guiding member 18 is slidingly moved along the puncturing cannula angle adjusting elongate hole 19A of the support plate 19 to set the puncturing angle so that the tip end of the puncturing cannula is located at a desired point of the tissue of the living body to be examined. Then, the fastening screw is fastened to fix the puncturing cannula guiding member 18 thereto. The puncturing cannula is inserted under such a condition. If the tip end of the puncturing cannula is set at the desired point, under the cannular inserted condition, the fastening outer sleeve 22 is rotated clockwise (or counterclockwise) to make the puncturing cannula introducing groove 22A aligned with the puncturing cannula introducing groove 21B of the puncturing cannula introducing member 21 as shown in FIG. 8. Then, the puncturing cannula is removed and made to pass through the puncturing cannula guiding slot 16, thereby removing the ultrasonic applicator.

If the tip end of the cannula is not located at the desired point, the puncturing cannula is removed and the puncturing angle is again set. At this time, the puncturing cannula is left set on the puncturing cannula guiding member 18.

As has been described above, in accordance with the ultrasonic probe of the first embodiment, the puncturing cannula guiding slot 16 is formed along a plane, included in the probe body 11, in the longitudinal direction intersecting with the application surface 12 of the applicator body 11, the ultrasonic transducer elements 13A and 13B are arranged on opposite sides of the slot 16, and the confronted ultrasonic transducer elements (divided ultrasonic transducer elements) 13A and 13B on the opposite sides of the slot 16 are actuated simultaneously with each other so that a sensitivity of the divided ultrasonic transducer elements 13A and 13B is substantially the same as that of the undivided ultrasonic transducer elements 13. Accordingly, it is possible to suppress a change in image quality caused by the provision of the puncturing cannula guiding slot 16 and at the same time to form an image of the puncturing cannula on the sectional view on the indicator means.

Thus, it is possible to readily and positively insert the puncturing cannula into the tissue of the living body to be examined at a disired point thereof.

Also, by using the puncturing cannula guiding mechanism A, the puncturing angle may be accurately set.

Also, in the case where the puncturing cannula guiding mechanism A is not used, although the puncturing angle would be inaccurate, the cannula may be inserted from anywhere in the puncturing cannula guiding slot 16.

Furthermore, by providing the puncturing cannula guiding slot 16 on the application surface of the ultrasonic applicator body 11, even during the insertion of the cannula, the ultrasonic applicator may be removed as the puncturing cannula is left unchanged.

Figure 9:
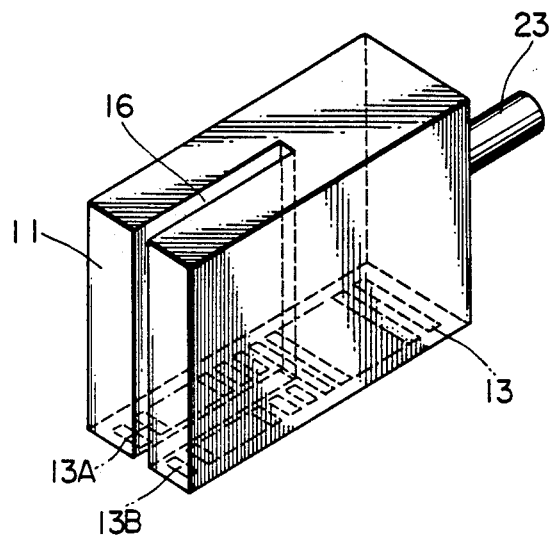
FIG. 9 is a schematic perspective view illustrating an ultrasonic probe in accordance with a second embodiment of the invention.

FIG. 9 is a schematic perspective view illustrating an ultrasonic applicator in accordance with the second embodiment of the invention.

As shown in FIG. 9, in the ultrasonic applicator in accordance with the second embodiment, an overall width of the pair of the divided ultrasonic transducer elements 13A and 13B shown in the first embodiment is made substantially the same as that of the undivided ultrasonic transducer elements 13. Thus, the width of the ultrasonic applicator is made thinner.

Although the sensitivity of the group of the thus divided ultrasonic transducer elements 13A and 13B is somewhat different from that of the group of the undivided ultrasonic transducer elements 13, it is possible to make the ultrasonic applicator thin enough to be applied to, for example, a part between ribs of a human being.

Figure 10:
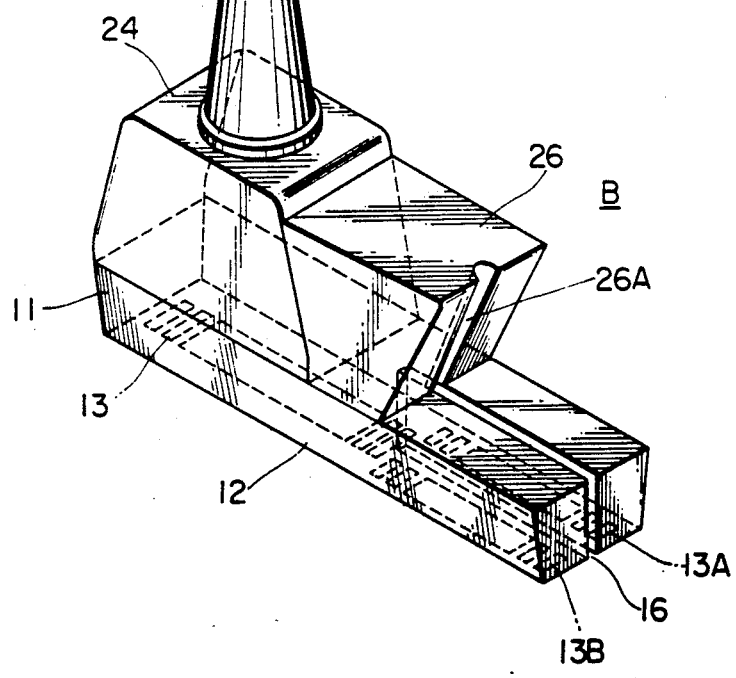
FIG. 10 is a schematic perspective view illustrating an ultrasonic probe in accordance with a third embodiment of the invention.

FIG. 10 is a schematic perspective view illustrating an ultrasonic applicator in accordance with the third embodiment of the invention.

As shown in FIG. 10, the ultrasonic probe in accordance with the third embodiment is provided with a puncturing cannula guiding mechanism B more specific and simpler than the puncturing cannula guiding mechanism A in accordance with the first embodiment in conformity with the tissue to be examined. Namely, the puncturing cannula guiding block 26 having a puncturing cannula introducing groove 26A is provided on the upper portion of the puncturing cannula guiding slot 16. The puncturing cannula introducing groove 26A is slanted at an angle of approximately 40° with respect to a line vertical to the application sided surface 12. The slant angle may be selected appropriately in accordance with the examination purpose of the tissue to be examined.

In accordance with the foregoing embodiment, the following advantages and effects will be obtained.

(1) The puncturing cannula guiding slot is formed in one plane within the ultrasonic applicator body along with the longitudinal direction of the applicator body while intersecting with the application surface of the applicator body, the ultrasonic transducer elements are arranged on both sides of the slot, and the ultrasonic transducer elements (divided ultrasonic transducer elements) arranged in face-to-face relation with respect to the slot are simultaneously actuated so that the sensitivity of the group of the divided ultrasonic transducer elements is made substantially the same as that of the group of the undivided ultrasonic transducer elements. With such an arrangement, it is possible to suppress a change in image forming quality due to the provision of the puncturing cannula guiding slot and to clearly form an image of the cannula in the sectional image on the indicator upon puncturing.

(2) Since the puncturing cannula guiding slot is provided so as to penetrate one side surface of the ultrasonic applicator body, the ultrasonic applicator may be removed during the puncturing operation while the puncturing cannula is kept unchanged.

(3) The puncturing cannula guiding mechanism is provided on the upper side of the puncturing cannula guiding slot, so that the puncturing angle may be set exactly at a desired point.

(4) Since, in accordance with the foregoing features (1) to (3), the puncturing cannula may be inserted exactly at a desired point of the tissue to be examined with ease, the positional alignment of the ultrasonic applicator may be facilitated, thereby effectively carrying out the puncturing operation.

It will be understood that the present invention is not limited to the foregoing specific embodiments but various modifications and changes are possible within the scope of the appended claims.

What is claimed is:

1. An ultrasonic applicator for insertion of a puncturing cannula, comprising an applicator body having a longitudinally extending lower application surface for contacting a living body and a plurality of ultrasonic transducer elements arranged on said lower application surface in parallel to one another in at least one predetermined row in a longitudinal direction of said lower application surface, at least some but no more than one half of said plurality of ultrasonic transducer elements being divided into two halves spaced apart from one another so that the two halves cooperate as a pair to form a single transducer element, said applicator body including means for defining a slot for guiding the puncturing cannula, said slot being formed as a thin parallelpiped like space extending from a center portion of said lower application surface between the two halves of respective pairs forming a single transducer element to an opposite upper surface of said applicator body.

2. The ultrasonic applicator according to claim 1, wherein an area obtained by adding the effective areas of the two halves of a respective pair forming a single ultrasonic transducer element is not less than the area of an undivided single transducer element.

3. The ultrasonic applicator according to claim 1, further comprising a puncturing cannula guiding means provided on the upper surface of said applicator body for guiding the puncturing cannula through said slot to a point to be examined.

4. The ultrasonic applicator according to claim 2, further comprising a puncturing cannula guiding means provided on the upper surface of said applicator body for guiding the puncturing cannula through said slot to a point to be examined.

* * * * *